US00PP29295P2

(12) United States Plant Patent
Hansen

(10) Patent No.: US PP29,295 P2
(45) Date of Patent: May 15, 2018

(54) ***HIBISCUS* PLANT NAMED 'AIRBRUSH EFFECT'**

(50) Latin Name: ***Hibiscus hybrid* (L.)**
Varietal Denomination: Airbrush Effect

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/731,015

(22) Filed: Apr. 7, 2017

(51) Int. Cl.
*A01H 5/02* (2018.01)

(52) U.S. Cl.
USPC ..... Plt./257

(58) Field of Classification Search
USPC ..... Plt./257
See application file for complete search history.

*Primary Examiner* — Annette H Para

(57) ABSTRACT

A new and distinct cultivar of winter-hardy, herbaceous, perennial, hybrid *Hibiscus* plant named 'Airbrush Effect' comprising a compact habit of multiple, well-branched, basal stems having flowers of a vibrant pink with salmon tones in concentrated speckles that appear like spray painted. The flowers have a small dark red eye and lighter pink center that increases in intensity and becomes darker and more concentrated as it radiates toward the petal tips. Flower shape is slightly cupped. The foliage is three-lobed, deeply dissected, and dark green colored.

1 Drawing Sheet

Botanical classification: *Hibiscus* hybrid (L.).
Variety denomination: 'Airbrush Effect'.

BACKGROUND AND ORIGIN OF THE PLANT

The present invention relates to the new and distinct winter-hardy, herbaceous, *hibiscus* plant, *Hibiscus* 'Airbrush Effect' hybridized under direction of the inventor on Jul. 25, 2012 at a wholesale perennial nursery in Zeeland, Mich. The new plant is a single seedling selection from among the cross between *Hibiscus* 'Pink Comet' U.S. Plant Pat. No. 13,751 times the proprietary unreleased hybrid known only by the breeder number 11-SRF-225 (not patented). The seeds were harvested in the fall of 2012 and the single unique plant among the resultant seedlings which passed the initial trial in the summer of 2014 was assigned the breeder code # 12-115-1. Both parents have a complex mixture of species in them, most likely comprising the species: *moscheutos* and *coccineus*. *Hibiscus* 'Airbrush Effect' was first asexually propagated in 2014 by sterile shoot-tip tissue culture at the same nursery in Zeeland, Mich. The resultant asexually propagated plants have been found to be stable and true to type in successive generations of asexual reproduction.

No plants of *Hibiscus* 'Airbrush Effect' have been sold by any name, either in this country or anywhere in the world, prior to the filing of this application, nor has any disclosure been made prior to the filing of this application with the exception of that which was sold or disclosed within one year of the filing of this application and was derived directly or indirectly from the inventor.

BRIEF SUMMARY OF THE PLANT

*Hibiscus* 'Airbrush Effect' differs from its parents as well as all other hardy herbaceous *hibiscus* known to the applicant in many traits. The most similar *hibiscus* in flower color known to the applicant are 'Balhiblu' U.S. Plant Pat. No. 15,054, 'Starry Starry Night' U.S. Plant Pat. No. 27,901 and 'Tie Dye' U.S. Plant Pat. No. 24,078. Compared with 'Balhiblu' the habit of the new plant is taller and more floriferous, and the petals more pink-colored and pleated at the veins. Compared with 'Starry Starry Night' the new flowers of the new plant are darker-colored rose toward the apex of the petals gradually lightening toward center, and 'Starry Starry Night' is darkest on the leading petal edge and the toward the center with greater contrast between the petal veins and lighter space between the veins, and the new plant is slightly shorter and more compact. Compared with 'Tie Dye' the new plant is shorter in habit, and the flowers of the new plant are deeper rose toward the petal apex. The female parent has more white in the petals and larger, more-contrasting flecking of deep red, the habit of the new plant is taller, and the foliage less rugose. Compared to the male parent the new plant has a taller habit, and the flowers of the male parent has a lighter pink flower and does not have the fine speckling of vibrant pink with salmon tones. The most unique feature of the new plant is the tightly specked flecking coloration of increasing concentration toward the apex of the petals.

*Hibiscus* 'Airbrush Effect' is a unique hardy herbaceous *hibiscus* with the following combined traits:

1. Winter-hardy, perennial with short compact habit of multiple, well-branched, basal stems.
2. Many rotate flowers over much of the summer season.
3. Flower petals having vibrant pink with salmon tones that appear spray painted with greater density of dots toward the apex, and lighter pink surrounding the small dark red eye zone.
4. Flower shape is slightly cupped.
5. Dark green, deeply-dissected, primarily tri-lobed foliage, rarely penta-lobed.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
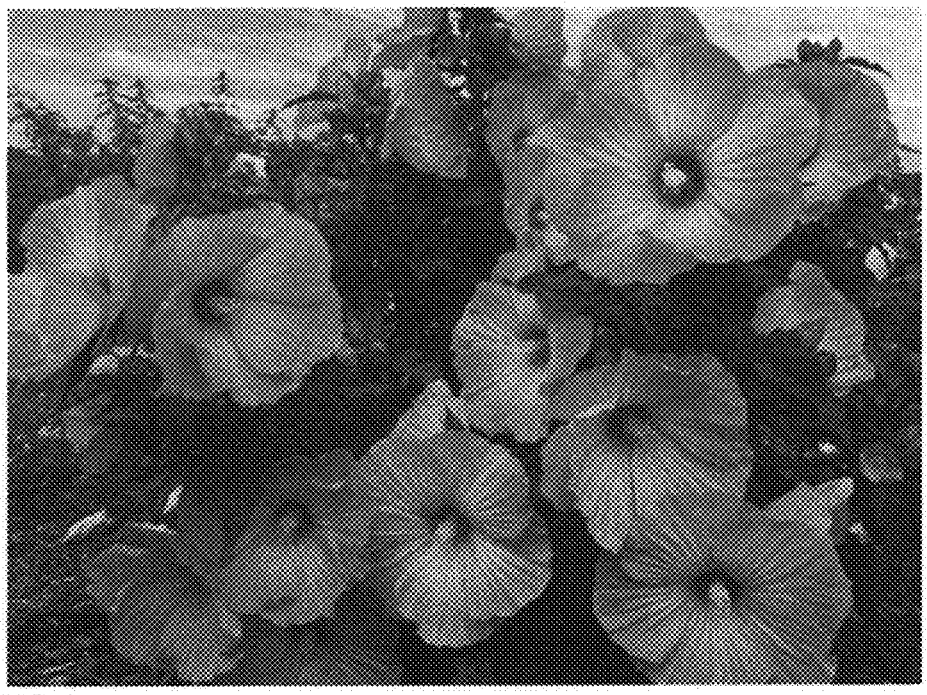
FIG. 1 shows a three-year-old plant in the landscape in mid-season.
Figure 2:
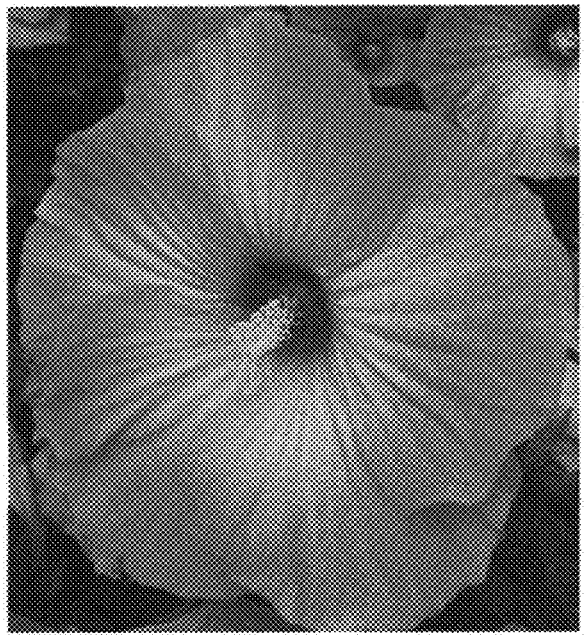
FIG. 2 shows a close-up of the flower.

The following descriptions and color references are based on the 2001 edition of The Royal Horticultural Society Colour Chart except where common dictionary terms are used. The new plant, *Hibiscus* 'Airbrush Effect', has not been observed under all possible environments. The phenotype may vary slightly with different environmental conditions, such as temperature, light, fertility, moisture and maturity levels, but without any change in the genotype. The following observations and size descriptions are of a three-year-old plant in the loamy-sand, open-field full-sun trials of a nursery in Zeeland, Mich. with supplemental fertilizer and water as needed. The plants are of natural habit without treatment of plant growth regulators, nor pinching at any time in the growth year.

Parentage: Female (seed parent) *Hibiscus* 'Pink Comet'; male (pollen parent) 11-SRF-225;

Propagation:

*Method*.—Stem cuttings and sterile shoot-tip plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about sixteen thick upright and heavily branched main stems producing a upright spreading mound to about 110.0 cm tall and about 132.0 cm wide; about eight primary branches per main stem protruding at about 45° from horizontal; flowering from base to top of plant with up to about thirty-three flowers per main stem.

*Stem*.—Terete, glabrous, glaucous; average about 88.0 cm tall and about 1.9 cm diameter at base.

*Stem color*.—Between RHS 144B and RHS 144A.

*Lateral branches*.—Average about eight per stem; terete, glabrous, glaucous; to about 34.0 cm long and 8.0 mm diameter, average about 16.0 cm long and about 4.0 mm diameter.

*Lateral branch color*.—Between RHS 144B and RHS 144A.

*Internode*.—About 28 nodes per stem below flowers, average internode length about 2.4 cm of unpinched plant below flowers.

*Internode color*.—Same as surrounding stem.

Foliage description: Alternate; coarsely and irregularly dentate; apical and lateral lobes acute; base rounded; glabrous; deeply cleft nearly to petiole, typically tri-lobed, rarely penta-lobed; slightly lustrous adaxial surface, matte abaxial surface; leaf blades to about 15.5 cm long and about 20.0 cm across, average leaf blade size 12.4 cm long and 14.0 cm wide; no fragrance detected;

*Foliage color*.—Mature adaxial nearest RHS 139A; mature abaxial between RHS 148A and RHS 148B; young adaxial between RHS 144A and RHS 144B; young abaxial between RHS 139C and RHS 139D.

*Veins*.—Palmate; lustrous; costate on abaxial.

*Vein color*.—Adaxial nearest RHS 152D; abaxial nearest RHS 145C.

*Petioles*.—Mostly terete, slightly flattened on adaxial side; glaucous; glabrous; average size about 5.3 cm long and 5.0 mm wide at base.

*Petiole color*.—Between RHS 144A and RHS 146D.

Flower description: Complete; actinomophic; upward to outward facing; rotate; lasting up to two days on plant; effective for about 8 weeks from late July to early September; no fragrance detected;

*Buds one day prior to opening*.—Ovoid with rounded apex and bluntly rounded base; carinate at sepal fusions; about 6.8 cm long and about 3.4 cm diameter in middle; sepals remaining close to petals to about 4.2 cm diameter.

*Bud color*.—Exposed petal color between RHS 61B and RHS 61C.

*Epicalyx*.—Typically up to 12 per flower; entire, micro-puberulent, dull surface abaxial and adaxial; linear with sharply acute apex and truncate base, arcuate upwards near apex; about 2.0 cm long and base of about 2.0 mm wide.

*Epicalyx color*.—Adaxial and abaxial between RHS 144A and RHS 146B.

*Sepals*.—Five; glabrous; acute apex; fused base; margin entire, edentate; abaxial and adaxial surfaces matte; about 4.0 cm long, fused in about the basal 2.0 cm, about 2.0 cm wide at fusion, connate forming campanulate star-shaped calyx.

*Sepal color*.—Adaxial base nearest RHS 148B; abaxial nearest RHS 148B; abaxial veins nearest RHS 148D; adaxial veins same as surrounding tissue.

*Flowers*.—Solitary, about 33 per main stem without pinching; slightly cupped petals; slightly upward to outwardly facing; average 21.0 cm across and 5.0 cm deep from center to edge of petals; larger in early part of flowering season; with lustrous deep red eye about 3.6 cm across.

*Petals*.—Five; glabrous, translucent; adnate to the androecium to form a column, imbricate to about 30% overlapping at widest part (petals overlapping about 30% of the petal portions on either side), palmately veined, primary and secondary veins impressed on adaxial and ribbed abaxial; shape: rounded with distinct claw and limb; margins: entire, edentate; apex: rounded; base: short claw-like; size: average about 14.5 cm across and about 11.0 cm long (larger in earlier part of flowering season).

*Petal color*.—Adaxial eye nearest RHS 53A, mid-section pale pink, lighter than RHS 62D between veins, outer perimeter with more concentrated speckling of between RHS 67C and RHS 67D; veins nearest RHS 67C; abaxial basal 2.0 cm between RHS 53A and RHS 53B, mid-section to apex between RHS 67D and RHS 68C, with veins nearest RHS 67C.

*Gynoecium*.—Single; partially enclosed in column. Column: glabrous except base micro-puberulent, lustrous; about 4.0 cm long and about 10.0 mm wide at base; Column color: between RHS 62D and RHS 63D; Style: micro-puberulent in region above column; protruding from column about 11.0 mm and split in distal about 8.0 mm into five branches; about 4.8 cm long and branch diameter about 1.0 mm; color lighter than RHS 62D; Stigma: typically five; globose, puberulent, about 2.5 mm in diameter; color nearest RHS 62D near center and nearest RHS 63D around perimeter; Ovary: Superior, about 7.0 mm across at base and about 7.0 mm tall; acute apex; color between RHS 145B and RHS 145C;

*Androecium*.—Filaments: numerous, about 100; about 6.0 mm long and about 0.3 mm diameter; attached along nearly the entire length of column; color nearest RHS 62D. Anthers: reniform; dorsifixed; about 2.5 mm long and 2.5 mm across and about 0.5 mm thick; color nearest RHS 158D; Pollen: abundant, globose, less than 0.1mm long; color lighter than RHS 196D.

Pedicel: Terete, glandular, hirsutulous to sparsely farinose; length from base of sepal to abscission point about 1.8 cm long, from abscission point to stem node about 2.5 cm long; about 3.0 mm wide; longer on early flowers and decreasing in distal flowers; color nearest RHS 138A above and below nearest RHS 146C;

Peduncle: Terete, glabrous, glaucous; about 42.0 cm long and about 3.5 mm diameter before flowers; with about 33 flowers per peduncle; color a blend between RHS 146A and RHS 147B with slight blush of RHS N186B in regions of intense light;

Fruit: Loculicidal capsule; pubescent along inner septa, glabrous outside; ovoid, with acute apex and rounded base; about 35.0 mm long and 26.0 mm diameter; color nearest RHS 200B when mature;

Seed: Minutely floccose, globose to slightly ovoid; about 3.2 mm in diameter; color nearest RHS N200A;

Resistance: *Hibiscus* 'Airbrush Effect' has not displayed any pest and disease resistance beyond that typical of hardy perennial *hibiscus*. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Airbrush Effect' as herein illustrated and described.

* * * * *